United States Patent [19]

Sugita et al.

[11] Patent Number: 4,985,543

[45] Date of Patent: Jan. 15, 1991

[54] LECTINS AND ANTIRETROVIRAL DRUGS CONTAINING THE LECTINS AS ACTIVE INGREDIENT

[75] Inventors: Norifumi Sugita, Tokyo; Koichi Niimura, Sayama; Yoshiharu Oguchi; Kunitaka Hirose, both of Tokyo; Kenichi Matsunaga, Tokorozawa; Minoru Oohara, Tokyo; Shigeaki Muto, Tokyo; Junji Kakuchi, Tokyo; Takao Furusho, Machida; Chikao Yoshikumi, Kunitachi; Masaaki Takahashi, Tokyo, all of Japan

[73] Assignee: Kureha Kagaku Kogyo Kabushiki Kaisha, Tokyo, Japan

[21] Appl. No.: 207,836

[22] Filed: Jun. 17, 1988

[30] Foreign Application Priority Data

Jun. 18, 1987 [JP] Japan .................................. 62-152092

[51] Int. Cl.$^5$ .......................... C07K 3/00; A61K 37/10
[52] U.S. Cl. ....................................... 530/396.; 514/8; 424/195.1
[58] Field of Search ............................ 530/396; 514/8; 424/195.1

[56] References Cited

U.S. PATENT DOCUMENTS 4,699,787  6/1987  Ueno et al. ............................ 424/95

OTHER PUBLICATIONS

Biological Abstract, vol. 68, 1979, Abstract No. 18024, Biological Abstracts Inc., Philadelphia, PA 18024.
Chemical Abstracts, vol. 110, No. 5, p. 306, Abstract No. 36478r.
Chemical Abstracts, vol. 110, No. 9, p. 332–333, Abstract No. 72147r.
Chemical Abstracts, vol. 84, p. 121, Abstract No. 174550d.
Finkelstein et al., Virology 69(2): 570–586, 1976.

Primary Examiner—John W. Rollins
Attorney, Agent, or Firm—Nixon & Vanderhye

[57] ABSTRACT

Disclosed herein are lectins extracted form a plant of the class Dicotyledoneae and an antiretoviral drug comprising as an active ingredient an effective amount of the lectins.

5 Claims, No Drawings

LECTINS AND ANTIRETROVIRAL DRUGS CONTAINING THE LECTINS AS ACTIVE INGREDIENT

BACKGROUND OF THE INVENTION

The present invention relates to a hemagglutinin, that is, lectins extracted from plant seeds, especially the plants of the class Dicotyledoneae, and the antiretroviral drugs containing such lectins as active ingredient.

In recent years new types of viral diseases such as B type hepatitis, adult T cell leukemia and AIDS (acquired immunodeficiency syndrome) have been attracted. Human being has combatted the viral diseases by means of vaccination and succeeded in eradicating such diseases as smallpox, yellow fever and polio. However, vaccination alone is not enough to cope with the diseases involving the problem of persistent infection or cryptogenic infection such as AIDS, and thus the development of an antiviral drug which is safe and highly efficacious has been expected.

The present inventors had previously proposed polysaccharides extracted from the fungi of Basidiomycetes, showing an anticancer effect. For instance, in British Patent No. 1,331,513 is disclosed polysaccharides obtained from a liquid extract of a mycelium of a fungus species of Basidiomycetes or from a cultured broth of said species, said polysaccharides being free or substantially free of impurities originally present in said liquid extract or in said cultured broth, and being characterized by being a water-soluble amorphous solid which is non-hydroscopic and non-dialyzable; gives a positive result when tested for the presence of glucose after hydrolysis with 1N sulphuric acid; gives negative results when subjected to the ferric chloride reaction for determining the presence of phenols and to the Fehling reaction for determining the presence of reducing sugars; gives positive results when subjected to the anisaldehydesulphuric acid reaction, the Molish reaction with α-naphthol, the anthrone-sulphuric acid reaction, the tryptophane-sulphuric acid reaction, the chromotropic acid-sulphuric acid reaction, the aniline-hydrochloric acid reaction, the resorcinol-hydrochloric acid reaction, the carbazole-cysteine-sulphuric acid reaction, the Tollens reaction and the thioglycol-sulphuric acid reaction; shows only one spot at the anode side when subjected to electrophoresis in a 0.05 mol. sodium borate solution for 90 minutes using a cellulose acetate membrane at 20–25 V/cm; and shows no antimicrobial action to bacteria, fungi and yeasts such as *Staphylococcus aureus, Escherichia coli, Bacillus subtilis, Aspergillus niger* and *Candida albicans*.

As a result of the present inventors' studies for providing a medicinal substance which is safe and has an excellent antiretroviral activity, it has been found that lectins obtained from the plants of the class Dicotyledoneae have a function to inhibit the activity of reverse transcriptase as well as an inhibiting activity against adsorption of human immunodeficiency viruses (HIV) on human lymphocytes. The present invention has been attained on the basis of such finding.

SUMMARY OF THE INVENTION:

In a first aspect of the present invention, there is provided lectins obtained from a plant of the class Dicotyledoneae, having the following properties:

(a) (i) positive results when subjected to the α-naphthol-sulfuric acid reaction, indole-sulfuric acid reaction, anthrone-sulfuric acid reaction or phenol-sulfuric acid reaction and Lowry-Folin process or ninhydrin reaction after hydrochloric acid hydrolysis, or (ii) positive results when subjected to the Lowry-Folin process or nihhydrin reaction after hydrochloric acid hydrolysis;

(b) an elementary analysis of 20–55% carboxy 3–9% hydrogen and 0.1–16% nitrogen;

(c) a pH of 6.0–7.0;

(d) to contain at least glucose and N-acetylglucosamine as sugar component and at least glutamic acid, aspartic acid and lysine as protein component;

(e) (i) absorption peaks at 3600–3200 $cm^{-1}$ and 1700–1600 $cm^{-1}$ or (ii) an absorption peaks at 1700–1600 $cm^{-1}$ in the infrared absorption spectrum;

(f) a molecular weight of $10^3 - 3 \times 10^6$ as measured by gel filtration chromatography; and (g) soluble in the aqueous solvent, and insoluble in chloroform, benzene and ether.

In a second aspect of the present invention, there is provided an antiretroviral drug comprising as an active ingredient an effective amount of lectins obtained from a plant of the class Dicotyledoneae.

DETAILED DESCRIPTION OF THE INVENTION

The lectins of the present invention are obtained from the plants of the class Dicotyledoneae and have a function for inhibiting the reverse transcriptase activity as well as an inhibiting activity against adsorption of a human immunodeficiency virus, and the antiretroviral drug according to the present invention comprises as active ingredient the lectins obtained from the plants of the class Dicotyledoneae.

The term "lectins" used in the present invention refers to the protein-bound polysaccharides or proteins having such functions as promoting cell agglutination, activating the cell division inducing function and raising cytotoxicity.

The plants of the class Dicotyledoneae from which the lectins of the present invention (hereinafter referred to as the present substance) can be obtained include all the plants belonging to Group 1, Group 2 and Group 3 of Dicotyledones in the Makela's classification (O. Makela: Ann. Med. Exp. Biol., FENN, 35, supl. II (1957); and R. Mori and T. Osawa: LECTIN, June 10, 1976, Kodansha). For example, in Group 1, the dicotyledons of the genus to which *Lotus tetragonolobus* and *Ulex europeus* belong, are exemplified, and from Group 2, those of the genus to which *Abrus precatorius, Abachis hypogaea, Bandeiraea simplifolia, Bauhinia purpunea, Calpuria aeggptiana, Femes formentarius, Glycine max, Maackia amurensis, Phaseolus lunatas, Phaseolus vulgaris, Ricinus communis, Robinia pseudocacia, Sophora japonica, Wistaria floridunda* and *Vicia cracca* belong, are exemplified. In Group 3, those of the genus to which *Canavalia ensiformis, Jack bean, Lens culinaris, Pisum sativum, Vicia faba, Cytisus sessilifolius, Labrurnum alpinum, Cerastrium fomentosus* and *Ulex europeus* belong, are exemplified.

Among the above-mentioned dicotyledons, those of the genera to which *Ulex europeus, Maackia amurensis, Glycine max, Jack bean* and *Lens culinaris* belong, are preferred. It is preferred to use the seeds of these plants.

The present substance can be obtained by extracting a plant of the class Dicotyledoneae with an aqueous solvent at 4° to 150° C. for 20 minutes to 20 hours, and subjecting the extract to refining treatment.

The aqueous solvent used for the extraction according to the present invention is selected from water and aqueous solutions containing a small amount, such as not more than 10%, of an organic solvent, acid, base or salt soluble in water. The extraction according to the present invention is carried out by the method selected from the group consisting of the water extraction, the organic-solvent extraction, the acid-solution extraction, the base-solution extraction, the salt-solution extraction and a combination thereof. As the organic solvent, methanol, ethanol, isopropyl alcohol and the like can be used. Hydrochloric acid, sulfuric acid, acetic acid and the like can be used as acid. The bases usable in the above-mentioned extraction include ammonia, sodium hydroxide, potassium hydroxide, sodium carbonate and the like. As the salt, sodium chloride, potassium chloride and the like can be used.

The extraction is usually carried out at a temperature of 4° to 150° C. for 20 minutes to 20 hours by using 5 to 200 times as much amount of extracting solution as the plant (seed) (dry basis).

The refining treatment is intended to remove low-molecular weight substances by such treatment as salting-out, affinity chromatography, dialysis, ultrafiltration, reverse osmosis, gel filtration, precipitation by use of an organic solvent, etc., or a combination of such treatments. Technologically, it is preferred to conduct either ultrafiltration, reverse osmosis or a combination thereof, which are membrane separation methods under pressure. In some cases, such treatment(s) may be conducted after salting-out.

Ammonium sulfate, common salt (sodium chloride), potassium chloride, barium carbonate and the like can be used as salting-out agent, ammonium sulfate being most preferred. After the salting-out treatment, it is necessary to carried out at least one treatment selected from dialysis, ultrafiltration, gel filtration and reverse osmosis.

For affinity chromatography, a column packed with such carrier as dextran, agarose, polyacrylamide gel or the like can be used, and the column may be used either as it is or after having fixed thereto a material having a sugar chain structure specific to lectin, which the material is refined by a chemical technique.

Dialysis is usually conducted by using a semipermeable membrane such as cellophane or collodion membrane.

Gel filtration is carried out by using a column packed with an adsorbent such as dextran, polyacrylamide or the like. The fillers commercially available under the trade names of Sephadex and Bio-Gel are usually used.

Ultrafiltration and reverse osmosis are the methods for fractionation using a membrane under pressure. The operation is usually carried out under a pressure of 0.5 to 5 kg/cm$^2$ in the case of ultrafiltration and 20 to 35 kg/cm$^2$ in the case of reverse osmosis.

Precipitation by use of an organic solvent is generally conducted by using such solvent as methanol, ethanol, iso-propanol, acetone or the like. If necessary, an ion exchange treatment may be combined with said operations.

The refined product is dehydrated by spray-drying, freeze-drying or other means and then worked into a final product.

The present substance obtained by extracting the plant with water or an aqueous solution containing a small amount of an organic solvent, acid or salt and subjecting the extract to refining treatment is preferably further treated with an aqueous alkaline solution and as a result, quite surprisingly, the antiretroviral effect of the thus treated substance is increased.

Such alkaline solution treatment is accomplished, for example, by treating the present substance with 5 to 200 times as much amount of a 0.01-5N, preferably 0.1-2N aqueous alkaline solution at a temperature of 40°-250° C., preferably 60°-200° C., most preferably 100°-150° C., for 5 minutes to 2 hours, preferably 10 minutes to one hour. Then, the treated solution is neutralized and subjected to a refining treatment selected from at least one of salting-out, dialysis, ultrafiltration, reverse osmosis, gel filtration, precipitation by use of an organic solvent and the like as mentioned above. The conditions to be used for such refining treatments are the same as described above. After this refining operation, the product is dehydrated by spray drying, freeze drying or other means.

The present substance obtained in the manner described above gives (i) positive results when subjected to the α-naphthol-sulfuric acid reaction, indole-sulfuric acid reaction, anthrone-sulfuric acid reaction or phenol-sulfuric acid reaction and Lowry-Folin process or ninhydrin reaction after hydrochloric acid hydrolysis (protein-bound polysaccharides), and (ii) positive results when subjected to the Lowry-Folin process or ninhydrin reaction after hydrochloric acid hydrolysis (proteins).

The elementary analysis of the present substance shows 20-55% carbon, 3-9% hydrogen and 0.1-16.0% nitrogen, and a pH of 6.0-7.5.

The present substance also contains at least glucose and N-acetylglucosamine as sugar component and at least glutamic acid, aspartic acid and lysine as protein component.

The infrared spectrum of the present substance shows (i) absorption of hydroxyl group in the region of 3600-3200 cm$^{-1}$ and absorption attributable to amide group in the region of 1700-1600 cm$^{-1}$ (protein-bound polysaccharides) and (ii) absorption attributable to amide group in the region of 1700-1600 cm$^{-1}$ (protein).

The present substance is soluble in aqueous solvents and insoluble in organic solvents. The "aqueous solvents" include water and the aqueous solutions containing water-soluble alcohols, acid, bases, etc. The "organic solvents" refer to such solvents as chloroform, benzene and ether.

The present substance is white or brown in color and has a molecular weight of $10^3-3\times10^6$ as measured by gel filtration chromatography.

In an acute toxicity test of the present substance in which the present substance was orally administered to the rats (Donryu strain) of 4-5 weeks old, having a body weight of 100-150 g at a dose of 1,000 mg/kg and their conditions were observed for seven days, all of the rats were alive in the seven-days observation period after the administration. The present substance is a safe material which is very low in toxicity and causes almost no harmful side effect.

It is known that generally a virus is adsorbed on a target cell and nucleic acid of the virus is injected into the cell and further integrated into the genome of the cell, through which process the virus is replicated. In the case of retrovirus, a process of transferring RNA, which is a nucleic acid derived from the virus, into DNA by the action of reverse transcriptase is necessary before the nucleic acid is integrated into the genome of the cell.

The present substance inhibits adsorption of HIV (human immunodeficiency virus) on human lymphocytes and succeeding infection thereof, and also inhibits the activity of reverse transcriptase. The actual effect of the present substance was investigated by a method in which HIV (human immunodeficiency virus) was treated with a 50–1,000 μg/ml conc. solution of the present substance at 0° C. for 2 hours, then washed, was applied to the MT-4 cells to infect them with the virus, and after 3-day culture, the number of the HIV antigen positive cells was counted. It was found that the HIV antigen positive cells have been substantially eliminated by the pretreatment with the present substance, which indicates the strong inhibitory effect of the present substance against adsorption of HIV on human lymphocytes. When the effect of the present substance on the reverse transcriptase activity was examined by using whole messenger RNA from rat liver as template, a strong inhibition against reverse transcriptase activity was shown by the addition of 500 μg/ml of the present substance.

These facts attest to the inhibiting activity of the present substance against viral infection, particularly against the infection of retroviruses having reverse transcriptase, and especial efficacy against AIDS caused by HIV infection.

In the case of azido-3'-dioxythymidine (AZT) which is already used as an antiviral drug, it has a side effect of inhibiting segmentation of even normal cells, whereas the present substance is a safe material which is extremely low in acute toxicity and useful as an antiviral drug since it shows an inhibiting activity against infection of viruses, especially retroviruses. Thus, the present substance is effective for the treatment of viral infectious diseases, especially retroviral infectious diseases such as AIDS in particular.

In use of the present substance as an ativiral drug, it can be offered in any desired form of preparation. Also, the preparation can be administered in various ways. Further, the present substance can be used in combination with other known antiviral drug such as AZT without lowering the nomal efficacy. Such combined use with other drugs is indeed quite recommendable.

In the case of oral administration, the preparation may take the form of tablet, granules, powder, capsule, etc., which may contain in their composition various types of adjuvant(s) usually used for the pharmaceutical compositions, such as binder, inclusion, excipient, lubricant, disintegrator, wetting agent, etc. In the case where the present substance is used as a liquid preparation for oral administration, the preparation may take the form of liquid medicine for internal use, shake mixture, suspension, emulsion, syrup, etc. It may take the form of a dry product which is dissolved in water when used. Also, such liquid preparations may contain the usually used additives and preservatives. In the case of injection, the composition may contain such additives as stabilizer, buffer agent, preservative, isotonizing agent, etc., and is offered in the form of unit-dose ampule or in the multiple-dose containers. Also, the composition may take the form of aqueous solution, suspension, solution, emulsion in an oleaginous or aqueous vehicle, etc. The active ingredient (the present substance) may be a powder which, when used, is dissolved in a suitable vehicle such as pyrogen-free sterilized water.

The antiviral drug according to the present invention is administered to man and animals either orally or parenterally. Oral administration includes sublingual administration, and parenteral administration includes injection such as subcutaneous, intramuscular and intravenous injection and instillation. The dosage of the antiviral drug according to the present invention is variable depending on whether the subject is man or animal and also according to the age, individual difference, condition of the disease and other factors, but usually in the case where the subject is man, the oral dose of the present substance is 0.1 to 1,000 mg, preferably 1 to 100 mg, per kg of body weight and day, which is taken in one to three portions.

The present substance is a material having a function to inhibit the activity of a reserve transcriptase and an inhibiting activity against adsorption of an HIV on human lymphocytes, and extremely low in acute toxicity and high in safety. The present substance is also effective for the treatment of viral infectious diseases, especially retroviral infectious diseases such as AIDS in particular.

The present invention is explained in more detail in the following Examples; however, it should be recognized that the scope of the present invention is not restricted to these Examples.

EXAMPLE 1

100 g of dry *Ulex europeus* was dissolved in 1 liter of physiological saline solution, stirred and extracted overnight at 4° C. and then centrifuged for separation into supernatant and sediment.

The resultant supernatant was added with ammonium sulfate to 30% saturation, stirred for about 2 hours and then centrifuged for separation into supernatant and sediment. The thus obtained supernatant was further added with ammonium sulfate to 80% saturation, stirred well and centrifuged. The sediment was collected and dialyzed against a physiological saline solution. The dialyzate was refined by a column packed with starch crosslinked with L-fucose by using epichlorohydrin. More specifically, the dialyzate was refined by using on an L-fucose-starch column washed well with a 5 mM phosphate buffer solution (pH 7.0) containing 0.15M common salt and then the column was washed with the same buffer solution. After elution of a large peak of non-active protein has ended, further elution was made with a 0.05M glycine-bydrochloric acid buffer solution (pH 3.0) containing 0.5M common salt to obtain the desired fraction. After removing the salts by ultrafiltration, the fraction was freeze-dried to obtain a white powder.

EXAMPLE 2

100 g of finely ground seed of *Maachia amurensis* was suspended in 1 liter of a physiological saline solution and the suspension was stirred overnight at 4° C. and then centrifuged to be separated into supernatant and sediment. The resultant supernatant was added with ammonium sulfate to 50% saturation, stirred for about 2 hours and centrifuged for separation into supernatant and sediment. The thus obtained supernatant was further added with ammonium sulfate to 80% saturation, stirred well and centrifuged. The formed sediment was collected and dissolved in a 0.001M phosphate buffer solution (pH 7.0) containing 0.15M common salt, and the solution was refined by using a column of Sepharose 4B-swine thyroid thyroglobulin glycopeptide and then the column was washed with said phosphate buffer solution. After initial elution of a large peak of non-active protein, the fraction having protein peak wa collected. After removing the salts by ultrafiltration, the fraction was freeze-dried to obtain a white powder.

EXAMPLE 3

100 g of de-fatted powder of soybean (*Glycine max*) was suspended in 500 ml of a physiological saline solution and stirred and extracted at room temperature for 1 to 2 hours. The extract solution was centrifuged and the supernatant was collected. The collected supernatant was added with ammonium sulfate at a rate of 30 g to 100 ml of said supernatant at 4° C., and the solution was stirred well and centrifuged. The sediment was removed and the supernatant was further added with 25 g of ammonium sulfate and the formed sediment was collected. The collected sediment was dissolved in a small amount of water and dialyzed against water and then against a physiological saline solution. The dialyzate was refined by using a column (4.0×30 cm) of sepharose-N-(ε-aminocaproyl)-β-D-galactopyranosilamine and then the column was washed with a physiological saline solution until the elution of non-active protein was finished. Further, by elution with a physiological saline solution containing 0.5% of D-galactose a fraction (lectin) having a high agglutinating activity was obtained. After sufficient dialysis against water, the product was freeze-dried to obtain a white powder.

EXAMPLE 4

200 g of finely ground and dried *Jack bean* was dissolved in 1 liter of 1M NaCl (pH 7.0) and extracted at 4° C. for 10 hours. The extract solution was centrifuged to be separated into supernatant and sediment. The resultant supernatant was added with ammonium sulfate to 30% saturation (pH 7.0), allowed to stand at 4° C. for 2 hours and then centrifuged. The sediment was removed and the residual supernatant was 80% saturated with ammonium sulfate (pH 7.0) and stirred at 4° C. for 6 hours. The mixture was centrifuged and the sediment was collected. This sediment was dissolved in a small amount of water and dialyzed against water for one hour and then against 1M NaCl (pH 7.0) for 10 hours. The dialyzate was subjected to Sephadex G-75 (4×50 cm) equilibrated with 1M NaCl at pH 7.0 and the column was washed well with the dialyzate solution.

By elution with 1M NaCl and 0.1M glucose, the objective material was obtained. The eluate was desalted by ultrafiltration and freeze-dried to obtain a white powder.

EXAMPLE 5

200 g of finely ground and dried *Lens culinaris* was dissolved in 1 liter of 1M NaCl (pH 7.0) and extracted overnight at 4° C. The extract solution was centrifuged to be separated into supernatant and sediment. The resultant supernatant was added with ammonium sulfate for 30% saturation (pH 7.0), allowed to stand at 4° C. for 2 hours and then centrifuged. The sediment was removed and the supernatant was 80% saturated with ammonium sulfate (pH 7.0) and stirred at 4° C. for 6 hours. This mixture was centrifuged and the sediment was collected. This sediment was dissolved in a small amount of water and dialyzed against water for one hour and then against 1M NaCl (pH 7.0) for 10 hours. The dialyzate was subjected to Sephadex G-75 (4×50 cm) equilibrated with 1M NaCl at pH 7.0 and the column was washed with the dialyzate solution.

By elution with 1M NaCl and 0.1M glucose, the objective fraction was obtained. The eluate was desalted by ultrafiltration and freeze-dried to obtain a white powder.

The physicochemical properties of the substances extracted from various species of pulse are shown in Table 1. In the table, the positive result of the phenolsulfuric acid color reaction indicates the presence of saccharides, the positive result of and the Lowrey-Folin reaction indicates the presence of peptide bond. As for the molecular weight, the molecular weight distribution of the fraction rich with the present substance as measured by the gel filtration method was shown.

EXAMPLE 6

The degree of inhibition by the present substances obtained in Examples 1–5 against reverse transcriptase specifically retained by the retroviruses was determined according to the following method.

10 mg of a freeze-dried sample of each of the said substances was dissolved in 10 ml of sterilized distilled water (concentration: 1 mg/ml).

Separately, 1 µl of 20 mM D.T.T. (dithiotheritol, produced by Sigma Co., Ltd.), 5 µl of a 5-fold concentrated enzyme reaction solution (250 mM tris-HCl (pH 8.3), 250 mM KCl and 40 mM $MgCl_2$), 1 µl of 3d NTP solution (1 mM dATP, 1 mM GTP and 1 mM dTTP, produced by Sigma Co., Ltd.), 2 µl of 100 ug/ml oligomer $(dt)_{12-18}$ (produced by PL-Biochemicals Co., Ltd.), 1 µl of messenger RNA (derived from normal rat liver, 1 µg/µl), 0.5 µl of RNase inhibitor (16 unit/µl, produced by Takara Shuzo Kabushiki Kaisha) and 1 µl of [$\alpha$-$^{32}$P] dCTP (up to 800 ci/mmol, 10 µci/µl, produced by Amersham Japan Co., Ltd.) were added into a 1.5 ml Eppendolf tube and the tube was placed in a 37° C. water bath.

5 minutes thereafter, 12.5 µl of the previously prepared solution of each said substance (concentration: 1 mg/ml) was added into the reaction tube. Then 1 µl of reverse transcriptase (7 unit/µl, derived from Rous associated virus, produced by Takara Shuzo Kabushiki Kaisha) was added and the mixture was reacted at 37° C. so that the final amount of the reaction solution would become 25 µl.

One hour thereafter, 5 µl of the reaction solution was infiltrated into the 2 cm×2 cm sheets of DEAE filter paper (produced by Toyo Roshi Kabushiki Kaisha). After air drying, each sheet was immersed in 10 ml of a 0.5M $Na_2HPO_4$ solution and [$\alpha$-$^{32}$P] dCTP which has been not used for DNA synthesis and remained on the sheet was washed away under shaking. (This operation was conducted 5 times at a five minutes' interval).

Thereafter, each of said DEAE paper sheets was placed in a glass vial containing 10 ml of a liquid scintillation cocktail (made by Amasham Japan Co., Ltd.) and the radioactivity of each sheet was counted for one minute (c.p.m.) by a scintillation counter (made by Aroka Co., Ltd.).

The reverse transcriptase activity inhibition rate (%) was determined from the following formula:

$$\frac{Co - Cs}{Co} \times 100$$

Co: Radioactivity of the sheet when not added with the present substance

Cs: Radioactivity of the sheet when added with the present substance

The Reverse transcriptase (RTase) activity inhibition rates (%) of the present substances are shown in Table 1.

EXAMPLE 7

The inhibiting activity of the present substances against adsorption of HIV (AIDS virus) on human lymphocytes was examined by the following method. (All the operations were conducted under an aseptic condition).

1 ml of a suspension of HIV (human immunodeficiency virus) and 1 ml of a solution of the present substance (800 μg/ml) were put into a test tube and the tube was placed still in ice. Two hours later, 1 ml of the virus suspension was taken out of the test tube and applied to the human lymphocyte-derived cell strain MT-4 (Jpn. J. Cancer Ros. (Gann), 28, 219–229 (1982)) so that the virus would be adsorbed on the cells at a multiplicity of infection (M.O.I.)≈2. After centrifuging at 2,000 r.p.m. for 10 minutes, the supernatant was discarded and the deposited MT-4 cells were suspended in RPMI 1640 (Gibco Laboratories, N.Y.) containing 20% of FCS so that the cell concentration would become $2 \times 10^5$ cell/ml.

The MT-4 cell suspension was pipetted in 100 μl portions into the 96-hole plates and cultured under the conditions of 5% $CO_2$ and 37° C. On the third day of culture, the HIV adsorbed cells and the non-adsorbed cells were calculated by the indirect fluorescent antibody technique.

The MT-4 cells were fixed by methanol treatment and reacted with the HIV infected patient antiserum at 37° C. 30 minutes thereafter, the cells were washed with PBS and reacted with FITC-bonded rabbit antihuman IgG at 37° C.

500 MT-4 cells were observed under a fluorescence microscope and the fluorescent positive cells were counted as HIV-adsorbed cells.

The HIV adsorption inhibition rate (%) was determined from the following formula:

$$HIV \text{ adsorption inhibition rate (\%)} = \frac{HIV\text{-adsorbed cells}}{HIV\text{-adsorbed cells} + \text{non-}HIV\text{-adsorbed cells}} \times 100$$

The results are shown in Table 1.

Preparation Example 300 mg of the present substance (Example 1) was filled in each of the #0 hard capsules by using an pressure type automatic filler to prepare the medicinal capsules.

TABLE 1

| Physicochemical properties of extracts | | | | | |
|---|---|---|---|---|---|
| | Material | | | | |
| Physicochemical properties of extracts | Compound of Example 1 | Compound of Example 2 | Compound of Example 3 | Compound of Example 4 | Compound of Example 5 |
| Material | Ulex europeus | Maackia amurensis | Glycine max | Jack bean | Lens culinaris |
| Color of material | White | White | White | White | White |
| pH | 6.5 | 6.4 | 6.6 | 6.4 | 6.5 |
| Absorption in infrared region ($cm^{-1}$) | 3600–3200 1700–1600 | 3600–3200 1700–1600 | 3600–3200 1700–1600 | 1700–1600 | 3600–3200 1700–1600 |
| Phenol-sulfuric acid cor reaction | + | + | + | − | + |
| Lowry-Folin color reaction | + | + | + | + | + |
| Molecular weight distribution | 10,000–100,000 | 10,000–100,000 | 10,000–100,000 | 10,000–100,000 | 10,000–100,000 |
| Elementary analysis | C: 44.9 H: 6.2 N: 15.2 | C: 40.3 H: 7.0 N: 14.6 | C: 49.5 H: 6.3 N: 15.2 | C: 35.7 H: 6.5 N: 16.0 | C: 42.6 H: 6.0 N: 15.7 |
| Solubility in choroform | Insoluble | Insoluble | Insoluble | Insoluble | Insoluble |
| Solubility in water (25° C.) | Soluble | Soluble | Soluble | Soluble | Soluble |
| RTase activity inhibition rate (*) | + | + | + | + | + |
| HIV adsorption inhibition rate (*) | +++ | +++ | +++ | +++ | +++ |
| Protein content (%) | 94.8 | 91.3 | 95.0 | 100.0 | 98.0 |
| Sugar content (%) | 5.2 | 8.7 | 5.0 | 0 | 2.0 |

Note
(*) +: 0–29%
++: 30–69%
+++: 70–100%

What is claimed is:
1. A lectin obtained from a plant selected from:
(1) *Lotus tetragonolobus* and *Ulex europeus;*
(2) *Abrus precatorius, Arachis hypogaea, Bandeirea simplifolia, Banhinia purpunea, Calpuria aegggptiana, Fomes formentarius, Glycine max, Maackia amurensis, Phaseolus lunatas, Ricinus communis, Sophora japonica, Wistaria floribunda* and *Vicia cracca;* and
(3) *Canavalia ensiformis, Lens eulinaria, Pisum sativum, Vicia faba, Jack bean, Cytisus sessilifolius, Laburnus alpinum, Cerastrium fomentosus* and *Ulex europeus,* each of (1), (2) and (3) being in the Makela classification, said lectin having the following properties:
(a) positive results when subjected to the α-naphthol-sulfuric acid, indole-sulfuric acid, anthrone-sulfuric acid or phenol-sulfuric acid reaction and, after hydrochloric acid hydrolysis, the Lowry-Folin process or the ninhydrin reaction;

(b) elementary analysis: 20–55% carbon, 3–9% hydrogen and 0.1–16% nitrogen;

(c) a pH of 6.0–7.0;

(d) the sugar component, when present, comprises at least glucose and N-acetyl-glucosamine and the protein component comprises at least glutamic acid, aspartic acid and lysine;

(e) infrared absorption spectrum peaks at $3,600-3,200$ cm$^{-1}$;

(f) a molecular weight of $10^3 - 3 \times 10^6$ as measured by gel filtration chromatography; and (g) soluble in water and aqueous solvent, and insoluble in chloroform, benzene and ether.

2. The lectin according to claim 1, which is obtained by extracting said plant with an aqueous solvent at 4°–150° C. for 20 minutes to 20 hours, and thereafter refining the extract.

3. The lectin according to claim 2, wherein said aqueous solvent is an aqueous solution of a water-soluble organic solvent, acid, base or salt.

4. The lectin according to claim 3, wherein said aqueous solution is an aqueous solution of ammonia, sodium hydroxide, potassium hydroxide or sodium carbonate.

5. The lectin according to claim 2, wherein the extract is further refined by salting-out, affinity chromatography, dialysis, ultrafiltration, reverse osmosis, gel filtration, or precipitation with an organic solvent.

* * * * *